(12) United States Patent
Rastogi et al.

(10) Patent No.: US 9,399,664 B2
(45) Date of Patent: Jul. 26, 2016

(54) PROCESS FOR PURIFICATION OF PNEUMOCANDIN

(75) Inventors: Kushal Rastogi, Banaglore (IN); Onkar Prakash Santan, Bangalore (IN); Nitin Sopanrao Patil, Bangalore (IN); Rakesh Bhaiyyaram Mendhe, Bangalore (IN)

(73) Assignee: Biocon Limited (IN)

( * ) Notice: Subject to any disclaimer, the term of this patent is extended or adjusted under 35 U.S.C. 154(b) by 211 days.

(21) Appl. No.: 13/637,920

(22) PCT Filed: May 17, 2010

(86) PCT No.: PCT/IN2010/000313
§ 371 (c)(1),
(2), (4) Date: Sep. 27, 2012

(87) PCT Pub. No.: WO2011/121599
PCT Pub. Date: Oct. 6, 2011

(65) Prior Publication Data
US 2013/0030149 A1    Jan. 31, 2013

(30) Foreign Application Priority Data
Mar. 29, 2010  (IN) ......................... 00861/CHE/2010

(51) Int. Cl.
*C07K 7/56*   (2006.01)

(52) U.S. Cl.
CPC ....................... *C07K 7/56* (2013.01)

(58) Field of Classification Search
None
See application file for complete search history.

(56) References Cited

U.S. PATENT DOCUMENTS

| 5,310,873 | A  | * | 5/1994  | Schmatz et al. | 530/317 |
| 6,809,177 | B1 | * | 10/2004 | Mukhopadhyay et al. | 530/317 |
| 8,101,712 | B2 | * | 1/2012  | Keri | C07K 7/56 530/323 |
| 2002/0028916 | A1 | | 3/2002 | Chandler et al. | |
| 2009/0291996 | A1 | * | 11/2009 | Korodi et al. | 514/410 |

FOREIGN PATENT DOCUMENTS

| WO | WO2008/048627 A1 | | 4/2008 |
| WO | WO 2008048627 A1 | * | 4/2008 |
| WO | WO2009/142761 A1 | | 11/2009 |

OTHER PUBLICATIONS

PCT International Search Report and Written Opinion, PCT Application No. PCT/IN2010/000313, Oct. 2010, 12 pages.

* cited by examiner

*Primary Examiner* — Louise W Humphrey
*Assistant Examiner* — Christopher Keller
(74) *Attorney, Agent, or Firm* — Schwegman Lundberg & Woessner, P.A.

(57) ABSTRACT

The process described herein discloses purification process of a secondary metabolite produced by fermentation route. The process involves selective removal of impurities at various stages of washings, charcoalization followed by crystallization. The product is closely related to class of echinocandins and is found to be potent antifungal compound & a key ingredient in the synthesis of antifungal drugs.

10 Claims, 1 Drawing Sheet

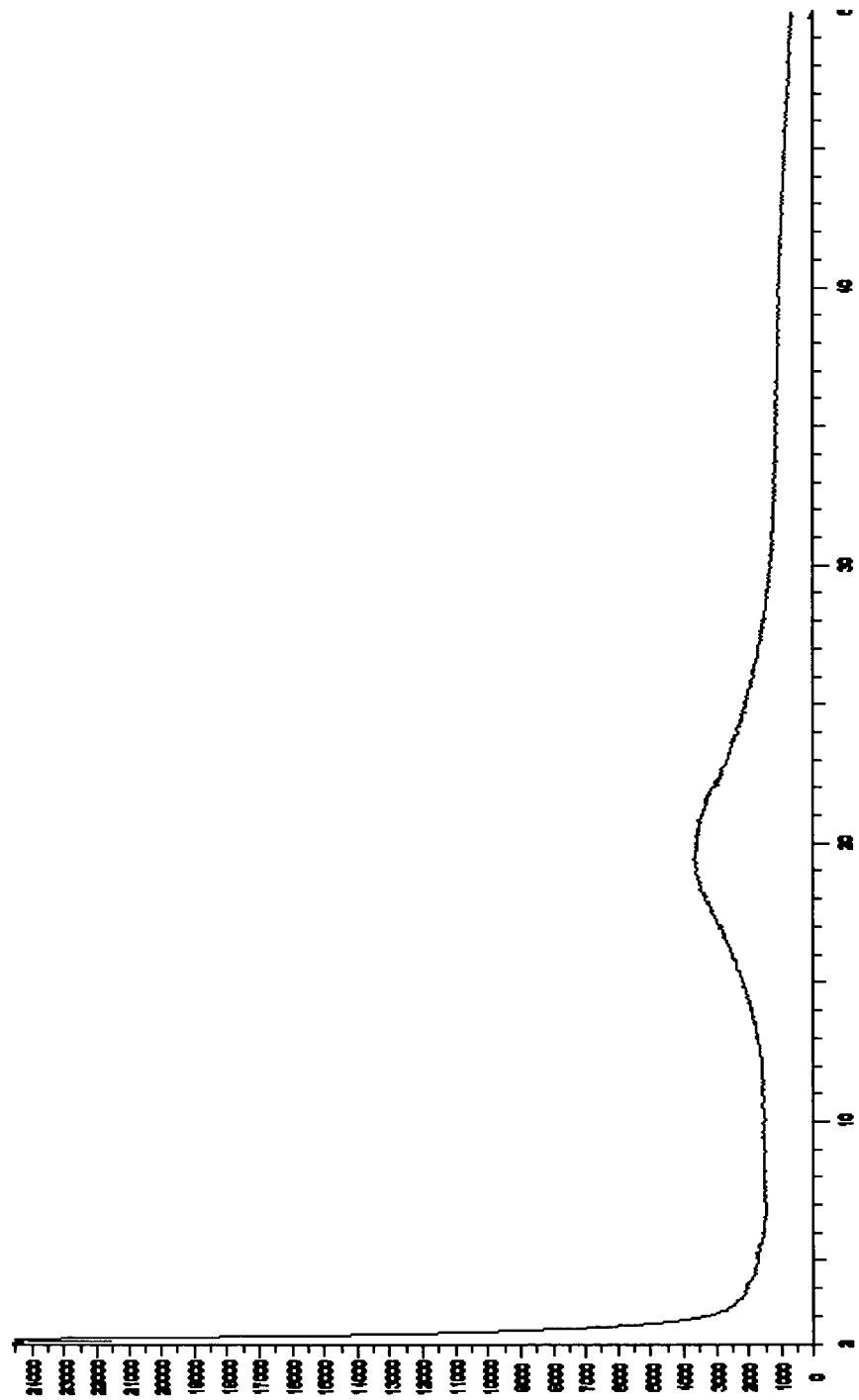
XRD of Pneumocandin – B$_0$

PROCESS FOR PURIFICATION OF PNEUMOCANDIN

FIELD OF INVENTION

The present invention is in relation to purification process of a secondary metabolite produced by fermentation route. The process involves selective removal of impurities at various stages of washings, charcoalization followed by crystallization. The product is closely related to class of echinocandins and is found to be potent antifungal compound & a key ingredient in the synthesis of antifungal drugs.

BACKGROUND OF INVENTION

The instant invention describes a novel process for purification of a naturally occurring secondary metabolite obtained from fermentation route. The product is closely related to echinocandins and is known to be a key intermediate to make antifungal agents. In particular, Pneumocandins are discussed in detail here. It is a cyclic hexapeptide with multiple hydroxyl groups and a hydrophobic dimethylmyristate tail connected via an amide bond to the alpha amino group of the hydroxylated omithine residue. According to ] R. E. Schwartz, D. F. Sesin, H. Joshua, K. E. Wilson, A. J. Kempf, K. E. Golden, D. Kuehner, P. Gailliot, C. Gleason, R. White, E. Inamine, G. Bills, P. Salmon, L. Zitano, Pneumo candins from *Zalerion arboricola*. I. Discovery and isolation, J. Antibiotics 45 (1992) 1853 and G. F. Bills, G. Platas, F. Pelaez, P. Masurekar, Reclassification of a pneumocandin-producing anamorph, *Glarea lozoyensis* gen. et sp. nov., previously identified as *Zalerion narboricola*, Mycological Research 102 (1998), Pneumocandin—$B_0$ can be produced by fermentation of *Glarea lozoyensis* (*Zalerion arboricola*). According to O. D. Hensens, J. M. Liesch, D. L. Zink, J. L. Smith, C. F. Wichman, R. E. Schwartz, J. Antibiotics 45 (1992) 1875 and A. Adeferati, 0. Hensens, E. T. T. Jones, J. Tkacz, J. Anti biotics 45 (1992) 1953, the organism can produce other echinocandins in addition to desired product Pneumocandin B0 including its isomers Pneumocandin $A_0$ and $C_0$. Structures of Pneumocandins are shown below.

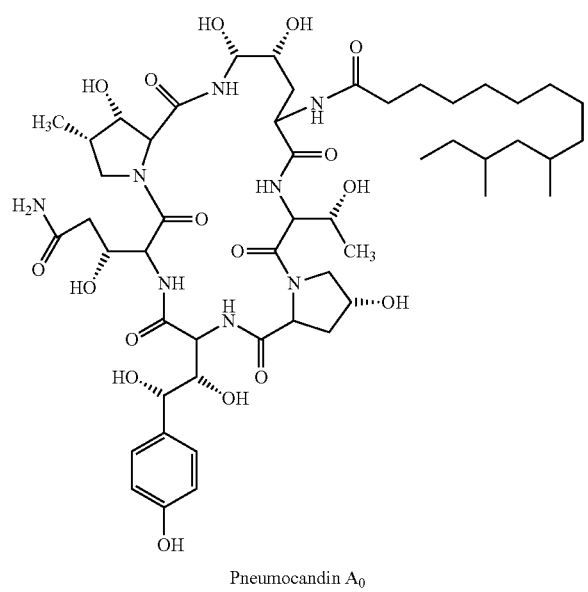

Pneumocandin $A_0$

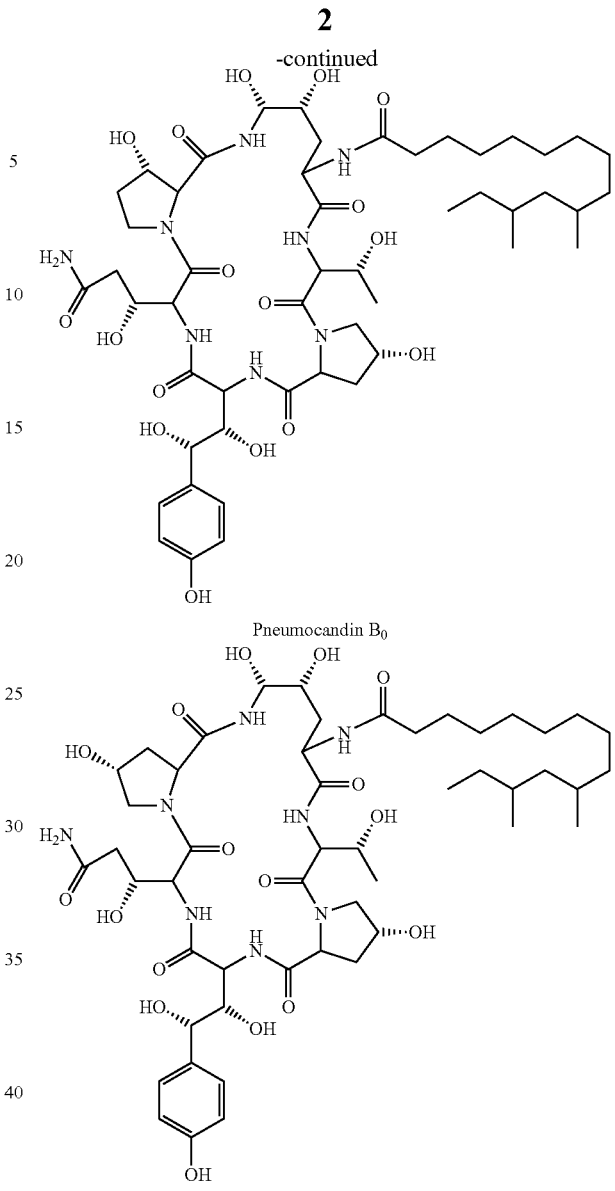

Pneumocandin $B_0$

Pneumocandin $C_0$

Structures of Pneumocandin—$B_0$ and its Isomers

The process followed for the purification of crude Pneumocandin-$B_0$ and related compounds involves solvent-solvent extractions, repeated column purifications and crystallizations which are tedious and need to look into simple and robust process. The instant process is simple and ease to opeate. The claiming process involves novel purification route involving washings with immiscible solvents or water, removal of UV inactive colored impurities and product selective crystallization. Process—1 has been found to have higher yields, better purity and lower raw material costs. The instant process inturn results in purity more than 90%.

STATEMENT OF THE INVENTION

The present invention provides a process for purification of pneumocandin having one or more polar impurities and one or more non-polar impurities comprising extraction of product from fermentation broth using suitable solvent and partially concentrated, washing with immiscible solvent, charcoalization, concentration and filtration, loading the solids obtained from step (d) in a column with an adsorbent, eluting with suitable solvents, concentration of product rich fractions and crystallization.

BRIEF DESCRIPTION OF ACCOMPANYING DRAWING

FIG. 1: XRD of Pneumocandin—$B_0$.

DETAILED DESCRIPTION OF THE INVENTION

The present invention is in relation to a process for purification of pneumocandin having one or more polar impurities and one or more non-polar impurities comprising;
  a) extraction of product from fermentation broth using suitable solvent and partially concentrated,
  b) washing with immiscible solvent,
  c) charcoalization,
  d) concentration and filtration,
  e) loading the solids obtained from step (d) in a column with an adsorbent,
  f) eluting with suitable solvents,
  g) concentration of product rich fractions and
  h) crystallization.

Pneumocandin is Pneumocandin-$B_0$.

In yet another embodiment of the present invention, suitable solvent for extraction of product from fermentation broth is selected from a group comprising n-butanol, sec-butanol, tertiary-butanol and n-propanol.

In still another embodiment of the present invention, the solvent is n-butanol.

In still another embodiment of the present invention, immiscible solvent is selected from a group comprising water, pet-ether and cyclohexane.

In still another embodiment of the present invention, the solvent is water.

In still another embodiment of the present invention, crystallization is carried out by solvent-antisolvent method.

In still another embodiment of the present invention, the solvent is selected from a group comprising methanol, n-propanol, iso-propanol, n-butanol, sec-butanol, tertiary-butanol and mixture thereof.

In still another embodiment of the present invention, the anti solvent is selected from a group comprising acetone, acetonitrile, pet-ether, cyclohexane, ethyl acetate, water and heptane.

In still another embodiment of the present invention, the solvent is n-butanol.

In still another embodiment of the present invention, the anti solvent is acetone.

In still another embodiment of the present invention, adsorbent is selected from a group comprising alumina and silica gel.

In still another embodiment of the present invention, the adsorbent is alumina.

In still another embodiment of the present invention, solvent for elution is selected from a group comprising methanol, n-propanol, iso-propanol, n-butanol, sec-butanol, tertiary-butanol, pentane, hexane, heptane, octane, ethyl acetate water and mixture thereof.

In still another embodiment of the present invention, polymorph obtained is amorphous as shown in FIG. 2.

In still another embodiment of the present invention, wherein purity is more than 90%.

The invention described herein discloses purification process of the cyclic lipopeptide type molecules for example echinocandin family having one or more polar impurities and one or more non-polar impurities, comprising following steps:
  a) extraction of product from fermentation broth using suitable solvent and partially concentrated,
  b) washing with immiscible solvent,
  c) charcoalization,
  d) concentration and filtration,
  e) loading the solids obtained from step (d) in to a column preloaded with an adsorbent,
  f) eluting with suitable solvents,
  g) concentration of product rich fractions and
  h) crystallization.

Process described herein is aimed at purification of naturally occurring secondary metabolite obtained from fermentation route. The process can be used in general for cyclo—peptide type molecules for example echinocandins. In particular the process aims at purification of Pneumocandin—$B_0$ which is a key product to obtain caspofungin diacetate, a known antifungal agent, through synthetic route. The instant Process involves selective removal of impurities, where product remains in one solvent and is treated with immiscible solvents for back wash, further it is treated with activated charcoal to remove significant amount of UV inactive colored impurities present from the start. This is followed by selective crystallization of product, while impurities largely remain in mother liquor and product precipitates. The first crystallization of the process results in amorphous form of Pneumocandin-$B_0$ with moderate purity (75-85%).

Further these crystals involves binding of product along with impurities onto a adsorbent. Typically N-alumina is used, but other variants of alumina or silica can also be used. After this, elution is carried out with solvent composition which is more selective towards impurities. This purification results in removal of other impurities and particularly $A_0$ in this step. This is followed by solvent composition which elutes moderate purity product, where some of other remaining impurities are removed.

Further, elution is carried out with product selective solvent which elutes high purity product. These high purity fractions are pooled and concentrated and crystallized to get high purity Pneumocandin-$B_0$ in solid form (>90%).

In particular, purification of Pneumocandin—$B_0$ of structure shown above is discussed.

The purification process involves extraction of the product from fermentation broth using suitable solvent, mostly alcohols viz. propanol, iso butanol, t-butanol, n-butanol. The Pooled extract layer is concentrated to about 30-50 g/kg stage under vacuum at 45-50° C. The next step is to remove polar and various other impurities present in concentrated extract. This is accomplished using a solvent or solvent composition which is immiscible. As n-bunaol is present in partially concentrated extracts, water can be taken for back wash. Typically ~2-3 volumes of water w.r.t. concentrated pooled extract is added and is mixed well and allowed for settling. n-butanol layer separates from aqueous layer along with product while large quantities of impurities are retained in aqueous layer. ~10-35% of purity increase can be obtained depending upon impurities in fermentation broth. Water wash can be repeated to achieve better possible purity. This n-butanol layer is diluted by adding additional quantity of n-butanol to make product concentration ~5-10 g/kg and treated with activated charcoal. Typically 0.5:1-5:1 (w/w) charcoal is used. The suspension is stirred well and filtered through celite bed followed by bed wash. UV inactive colored impurities are adsorbed in activated charcoal which further gets adsorbed on celite bed providing removal of non UV impurities. Also some UV active impurities gets adsorbed by celite giving chromatographic purity increase of about 10%. The n-butanol product layer is concentrated to about 30 g/kg stage.

The next step of purification involves crystallization. The crystallization described herein utilizes controlled addition of anti-solvent and cooling both. Solvent can be any of among methanol, propanol, iso-propanol, n-butanol, t-butanol, iso-butanol etc. and antisolvent can be any of among acetone, acetonitrile, ethyl acetate, water etc whereas preferably acetone is used.

Concentrated pooled product layer after purification steps as discussed above, is taken in a jacketed vessel for crystallization. Slow addition of antisolvent is initiated at room temperature. Flow rate is adjusted using a pump in such a way that 5 volumes of antisolvent is added over 4-6 hours. After 2-3 volumes addition of antisolvent, solution reaches close to saturation point at RT room temperature. At this moment, cooling is started and temperature is brought down to 0-10° C. while continuing addition of antisolvent. The crystallization step is sensitive towards initial product concentration, addition rate of antisolvent and cooling. Fast addition may yield to precipitate the impurities too, while slow addition may yield to wet paste instead of solid powder. Vacuum filtration is used to separate the solids from the mother liquor. Solid product is dried under vacuum at 40° C. for 24 hours. Depending upon the input purity of material, successive crystallization can be done to achieve further purification but it is observed that purification beyond 75-85% becomes extremely difficult.

Solids obtained from above step with purity 75-85% of Pneumocandin—$B_0$ co-exists with its isomers $A_0$ and $C_0$ and other closely related impurities. Separation of these impurities is difficult using simple unit operations like crystallization. Repetitive crystallization offers a very slight increase in purity at a significant loss of product. Conventionally it is required to have chromatographic preparative runs to isolate the $B_0$. Also, it is known that only normal phase chromatography with very specific mobile phase gives resolution between $A_0$, $B_0$, $C_0$ and other related impurities. The instant Process further involves novel method to further purification to obtain high purity (greater than 90%) of Pneumocandin $B_0$. The process involves loading of moderate purity (~75-80%) Pneumocandin—$B_0$ on an adsorbent. Adsorbent can be chosen among variants of Alumina or silica gel. Neutral alumina is particularly discussed in detail here. At this step, product along with impurities binds to the adsorbent bed. After this, selective removal of impurities is carried out by varying composition of the solvents. First solvent composition selective towards impurities is chosen to selectively elute impurities rich fractions, and then composition selective towards product is chosen to selectively elute high purity product fractions.

Solvents for the elution choosed among methanol, n-propanol, iso-propanol, n-butanol, t-butanol, sec-butanol, ethyl acetate, hexane, heptane and water etc. The study showed that water-rich eluent is highly selective for related impurities. It was observed that water rich eluent with small quantities of methanol is more selective towards $A_0$ isomer and iso-propanol rich solvent with hexane, (typically 80/20 v/v); is more selective towards $C_0$. Though it was found that certain composition of ethyl acetate, methanol water was more selective towards related impurities.

Different ratios of N-alumina with respect to product were tried and 30:1 ($w_{Alumina}/w_{product}$) ratio was found to be optimum for better yields and purity. Higher ratio of alumina requires more quantity of solvents to elute. The same percentage of product as in case of 30:1. Lower ratios of N-alumina result into loss of product.

To start with, N-alumina (30:1 w/w) is packed in a glass column to make a uniform bed. At production scale, nutsche filter can be used for bed packing. crystals obtained from previous step is dissolved in methanol to make product concentration ~15-40 g/L. This is loaded on the N-alumina bed. Small amount of flow through is obtained which shows only 1-2% of product loaded.

After this, selective elution of impurities is initiated. Typically one column volume of water is passed through the bed which takes out mainly related impurities and some $A_0$. This is followed by selective elution of other impurities. Typically gradient mixture of methanol-water is used for 5-8 column-volumes which takes almost all of related impurities and a greater extent of $A_0$. Finally product—$B_0$ with moderate purity (~80-84%) elutes and is collected separately. After selective elution of these impurities, 100% methanol is used for elution. It is most selective towards product as almost all related impurities and significant amount of $A_0$ is already eluted, product starts eluting with very high purity. 10-15 such fractions are eluted and collected separately. The purity of initial fractions ranges between 88-90%, while later fractions purity varies between 90-95%. These high purity fractions are pooled and concentrated to about 60-100 g/kg stage. Further this concentrate is crystallized using slow addition of acetone as antisolvent at temperature 0-10° C. as discussed in earlier.

The details of method are exemplified with the help of examples given below. However it should not be construed that the scope disclosure is limited to the examples.

EXAMPLES 20 kg of fermentation broth containing about 31 gm product—Pneumocandin $B_0$ was extracted using 8 Kg of n-butonal.

Example-1

853 gm of n-butanol extract layer consisting of 4.3 gm of product at purity 22.8% was taken and concentrated to 30 g/kg stage. This concentrate was washed with water 1:1 (w/w) basis. n-butanol layer obtained showed 4.1 gm of product with purity 44.9%. This n-butanol layer was pooled with another n-butanol layer (344 gm) with 4.93 gm of product at purity 26.7%. This pooled n-butanol layer was concentrated to ~30 g/kg stage followed by second stage water wash at 3:1 (w/w) basis. The n-butanol layer separated post water wash weighed 252 gm with product 8.4 gm (92.8%) at purity 60%. Aqueous layer weighed 923 gm with 0.407 gm (4.5%) product only at purity of 2.7%.

35 gm n-butanol layer was taken out of 252 gm n-butanol obtained above. Analysis showed 1.15 gm of product at concentration of ~33g/kg and purity ~60%. 0.5 gm of activated charcoal was added to this and was stirred for 1 hour. Separately 15 gm of celite was taken and slurry was made using n-butanol. Bed of celite was packed on Buchner funnel and charcoal suspension was loaded on this celite bed so that charcoal along with UV-inactive impurities gets adsorbed on the celite surface. Filtrate (140 ml) consisted of 1.1 gm (95%) with purity 70.1%. Further bed was given wash with n-butanol (50 ml) which showed 0.078 gm (~5%) at purity 68.5%. These two were pooled (190 ml) and used for crystallization.

Pooled filtrate and bed wash as obtained above (1.15 gm of product at purity ~69%) was concentrated to ~30 g/kg stage i.e. ~40 ml. Acetone was added drop by drop to the n-butanol-product solution. Flow rate of acetone was kept at 0.66 ml/min. After 3 volumes of addition of acetone, cooling of reaction mass was started. Temperature was started precipitating. Further addition of acetone was continued till 320 ml of acetone was added. Finally product was filtered out. The final product was brownish white in color. HPLC analysis showed 1.017 gm (88%) of product with purity 78.6%. XRD analysis showed it to be complete amorphous form.

Example-2

To make purification process robust, crystallization at lower purity of starting material was studied. Lower purity at crystallization stage may arise due to presence of greater percentage of impurities at the extract stage or due to improper treatment at washing and/or other purification steps. It has been observed in such a case additional crystallization may be required.

240 gm of n-butanol extract layer consisting of 4.97 gm of product at purity of 22.8% was taken. This was concentrated to product concentration of ~30g/kg stage and was given a water wash with 1:1 (w/w) basis. N-butanol layer post water wash showed 4.85 gm (97.6%) of product with purity of 38%. This was diluted to 395 gm with n-butanol to make product concentration ~10g/kg.

For charcoalization, 0.5:1 (w/w) of charcoal was taken and mixed with product for ~1hr. This was filtered on celite bed using 15:1 (w/w) of celite. 95% product was obtained in filtrate and 5% in bed-wash.

Filtrate and bed wash were pooled and crystallized similar to Example-1. Product (solid) obtained after $1^{st}$ crystallization showed 3.56 gm of product with purity 58.5%. Post $2^{nd}$ crystallization, 2.84 gm product was obtained with 67% purity. It required $3^{rd}$ crystallization to achieve 81.23% purity with final 1.98 gm product.

It has been observed that crystallization is one of the most critical step of purification Process-1. Antisolvent addition rate, quantity, introduction of cooling, initial load concentration and purity, nature of impurities all impact the performance and hence the results of crystallization. For example, at very high rate of antisolvent, product along with impurities precipitates, so purification does not happen that good. Further at fast antisolvent addition, more non UV-impurities precipitates, which may not be detected in HPLC purity but visibly looks very dark. Similarly, if cooling is started at very early stage when product is concentrated, precipitation starts very quickly resulting into similar phenomenon as discussed with faster antisolvent addition. Further, if addition rate is very slow, it does not crystallizes in a proper way and yields in a cake formation or fluffy mass on filtration instead of fine powder. It has also been studied that crystallization at 0-3° C. gives higher yields as compared to 8-10° C. due to further decreased solubility of product.

Example: Process 2

Product Pneumocandin-$B_0$ obtained from process-1 was used for further purification to obtain high purity (>90%) of Pneumocandin—$B_0$. 1.5 gm of solid product was taken and was dissolved in methanol such that product concentration becomes ~25g/L. Load was analyzed by HPLC and % area of product and impurities were as following:—Impurity T (RRT 0.33): 0.68%, $A_0$: 5.57%, $B_0$: 77.99%, Related Impurity—R (RRT 1.05): 4.42%, $C_0$: 5.97%.

45 gm of N-alumina was taken and bed was packed in a glass column. Bed dimensions were—diameter: 4 cm, height: 3.5 cm. Product was loaded onto this bed and flow through was collected. Flow through showed only 1.3% of the product with purity 76.92%.

Now selective elution of impurities was carried out as shown in FIG. 2. At first, 1 column volume elution with 100% water is carried out. This takes mainly impurity T (RRT 0.33) and impurity $A_0$, while little of product. HPLC analysis showed 5.57% of T, 26.23% of $A_0$ and 41.5% of $B_0$, while product loss was only 4.6%. % Area of R and C0 was 1.2% & 2.5% respectively.

This was followed by elution with methanol/water 25/75% (v/v). Typical composition of a fraction was ~8% T, ~12% $A_0$, ~60% $B_0$, ~2% R and ~4% $C_0$, while total product loss was only 1.5% in 6 column volumes.

Next one column volume was eluted with methanol-water 50/50% (v/v). This favors elution of other impurities along with the product resulting into moderate purity of product. Fraction analysis by HPLC showed ~8% $A_0$, 83.88% $B_0$ and 3% R, while T and $C_0$ were almost absent. Product loss in this fraction was only 0.51%.

Next 15 column volumes were eluted with 100% methanol and were collected separately. First fraction had 85.08% purity and second fraction had 86.5% purity. Fractions 3-5 had purity of ~88.3%, fractions 6-10 had purity of ~90-91.8% while 11-14 had 92-93.7% purity. After this, decreasing trend of purity was observed. Fraction 15 showed 91.99% purity.

Pooled fractions 1-14 showed in total 54.6% of the product with purity 90.21%. These pooled fractions were concentrated to ~25 ml and concentrate was transferred to a jacketed vessel. Acetone was used as antisolvent and crystallization was carried out as described earlier. Final product was filtered and dried under vacuum as described above. The final product was white in color and complete amorphous in form. HPLC analysis showed 91.37% purity of product—Pneumocandin $B_0$.

Although Process-1 and Process-2 are described for product Pneumocandin-$B_0$, but it is understood that such techniques can be used for purification of other molecules obtained from fermentation which are similar to lipo-peptides, particularly echinocandins family. The keys to the invention in Process-1 & Process-2 are selective removal of impurities, while product remains in one solvent from start to end. Process-1 has advantages over reported purification processes in terms of avoiding of repetitive back extraction and concentration steps with or without liquid-liquid extraction, which involves higher operating and raw materials cost along with significant losses of product. Process-1 discloses controlled crystallization of product which selectively precipitates the product. Process-1 discloses a novel way of purification where product remains in only one solvent from start to end, which improves yield, eases recovery of solvents as well as reduces the raw material costs. It has been found that process-1 has an overall yield of 55-70% (with respect to broth) with final product purity 75-82%. Process-2 has an overall yield of 45-55% with final product purity 90-93%.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

We claim:

1. A process for purification of pneumocandin $B_0$ with at least 90% purity, the process consisting of:

a) extracting pneumocandin $B_0$ from the fermentation broth using an organic solvent and partially concentrating the extract to obtain concentrated extract, wherein the solvent is selected from the group consisting of n-butanol, sec-butanol, tertiary-butanol, n-propanol and any combinations thereof;
b) washing the concentrated extract with a second solvent selected from the group consisting of water, petroleum ether and cyclohexane to obtain an organic layer;
c) charcoalizing and filtering the organic layer through a celite bed to obtain a filtrate;
d) crystallizing the filtrate to obtain a solid, wherein the crystallizing is carried out by solvent-antisolvent method, wherein the solvent is selected from group consisting of methanol, n-propanol, iso-propanol, n-butanol, sec-butanol, tertiary-butanol and any combinations thereof and the antisolvent is selected from group consisting of acetone, acetonitrile, pet-ether, cyclohexane, ethyl acetate, water and heptane or any combinations thereof;
e) loading the solid in a column with an adsorbent;
f) eluting with 100% water first, followed by alkanol/water, followed by 100% alkanol to obtain eluted pneumocandin $B_0$; and
g) concentrating and crystallizing the eluted pneumocandin $B_0$ to obtain the pneumocandin $B_0$ with at least 90% purity.

2. The process as claimed in claim 1, wherein the organic solvent is n-butanol.

3. The process as claimed in claim 1, wherein the second solvent is water.

4. The process as claimed in claim 1, wherein the crystallizing solvent is n-butanol.

5. The process as claimed in claim 1, wherein the antisolvent is acetone.

6. The process as claimed in claim 1, wherein adsorbent is selected from group consisting of alumina and silica gel.

7. The process as claimed in claim 6, wherein the adsorbent is alumina.

8. The process as claimed in claim 1, wherein the alkanol is selected from group consisting of methanol, n-propanol, iso-propanol, n-butanol, sec-butanol, and tertiary-butanol.

9. The process as claimed in claim 1, wherein the pneumocandin is amorphous pneumocandin.

10. A process for purification of pneu ocandin $B_0$ with at least 90% purity, the process comprising:
a) extracting pneumocandin $B_0$ from the fermentation broth using a first organic solvent selected from group comprising n-butanol, sec-butanol, tertiary-butanol and n-propanol, or any combinations thereof, and partially concentrating the extract to obtain concentrated extract;
b) washing the concentrated extract with a second solvent selected from the group consisting of water, petroleum ether and cyclohexane to obtain an organic layer;
c) charcoalizing and filtering the organic layer from step b) through a celite bed to obtain a filtrate;
d) crystallizing the filtrate from step c) to obtain a solid, wherein the crystallizing is carried out by solvent-antisolvent method, wherein the solvent is selected from group consisting of methanol, n-propanol, iso-propanol, n-butanol, sec-butanol, tertiary-butanol and any combinations thereof and the antisolvent is selected from group consisting of acetone, acetonitrile, pet-ether, cyclohexane, ethyl acetate, water and heptane or any combinations thereof;
e) loading the solid from step d) with an adsorbent;
f) eluting the column from step e) with 100% water first, followed by alkanol/water, followed by 100% alkanol to obtain eluted pneumocandin $B_0$, wherein the alkanol is selected from group consisting of methanol, n-propanol, iso-propanol, n-butanol, sec-butanol, and tertiary-butanol; and
g) concentrating and crystallizating the eluted pneumocandin $B_0$ to obtain the pneumocandin $B_0$ with at least 90% purity.

* * * * *